United States Patent [19]

Buonicore

[11] Patent Number: 4,549,363
[45] Date of Patent: Oct. 29, 1985

[54] APPARATUS FOR HOT DEGASSING RESIDUAL OLEFIN OXIDE FROM STERILIZED PRODUCT

[75] Inventor: Anthony J. Buonicore, Fairfield, Conn.

[73] Assignee: Buonicore-Cashman Associates, Inc., Bridgeport, Conn.

[21] Appl. No.: 576,434

[22] Filed: Feb. 2, 1984

[51] Int. Cl.$^4$ ............................................. F26B 19/00
[52] U.S. Cl. ...................................... 34/216; 34/233; 422/34
[58] Field of Search ................. 34/203, 232, 233, 216; 422/34, 116, 292

[56] References Cited

U.S. PATENT DOCUMENTS

| | | | |
|---|---|---|---|
| 517,700 | 4/1894 | Kimball | 34/232 |
| 524,598 | 8/1894 | Moore | 34/232 |
| 548,445 | 10/1895 | Morton | 34/232 |
| 1,587,041 | 6/1926 | Secord | 34/232 |
| 2,045,429 | 6/1936 | Willshaw et al. | 422/116 |
| 3,225,455 | 12/1965 | Waddelle | 34/233 |
| 3,326,114 | 6/1967 | Wolfe et al. | 422/292 |
| 3,616,548 | 11/1971 | Nichols | 34/233 |

OTHER PUBLICATIONS

Kereluk et al., "Ethylene Oxide Sterilization", J. Hosp. Res., vol. 7, pp. 7-75, (1969).
Gunther, "Absorption and Desorption of Ethylene Oxide", Amer. Journal of Hospital Pharmacy, vol. 26, pp. 45-49, (1969).
Ernst et al., "Toxic Residuals" in the Study of the Requirements, Preliminary Concepts and Feasibility of a New System to Process Medical/Surgical Supplies In the Field, U.S. Army Medical R&D Command, Washington, D.C., Contract No. DADA-17-70-C-0072 (1971), pp. 1-8, 14-18, 40-57, 76-79, 93-97, 151-156, 177-188, & 210-222.
Roberts et al., "Ethylene Oxide Sterilization" (Letter to the Editor), Anaesthesia, vol. 27, No. 2, 237 (1972).
Bruch, "Sterilization of Plastics: Toxicity of Ethylene Oxide Residues", Chapter 4 in *Industrial Sterilization*, Phillips, G. Briggs and W. S. Miller, Eds., Proceedings of International Symposium, Amsterdam, Duke University Press, Durham, North Carolina (1972).
Churinetz et al., "Ethylene Oxide Facility Design and Ventilation", Chapter 17 in *Ethylene Oxide Worker Safety Issues* Seminar Proceedings, Jorkasky, Jr., Ed. HIMA Report No. 82-2, Chicago, Ill. (1982).

*Primary Examiner*—Charles Hart
*Attorney, Agent, or Firm*—Fleit, Jacobson, Cohn & Price

[57] ABSTRACT

A cell for degassing of residual olefin oxide from an olefin oxide sterilized product. The product is fed through the cell on a gravity conveyor using a combination of heat, retention time and air change rate optimized for a particular product. A pallet containing the product to be degassed rolls to a preselected position within the cell. The pre-selected position is established by automatically controlled stops appropriately located on the gravity conveyors. The cell is dedicated to a specific sterilizer product load and can be arranged in a modular fashion with a minimum internal volume.

12 Claims, 3 Drawing Figures

4,549,363

APPARATUS FOR HOT DEGASSING RESIDUAL OLEFIN OXIDE FROM STERILIZED PRODUCT

BACKGROUND OF THE INVENTION

Olefin oxide gas sterilization of products made of such materials as rubber and plastics including polyvinyl chloride, polypropylene and polyethylene, using either pure ethylene oxide or propylene oxide, or an admixture with an inert diluent such as a fluorocarbon or carbon dioxide, is typically utilized for treating products which cannot withstand heat sterilization. Sterilization aids in the elimination of viable microorganisms or their endotoxin byproducts and decreases their associated infectious disease syndromes. After the sterilization period is completed, gas in the chamber is discharged to the atmosphere through an air pollution control device and the sterilized product removed. Due to the highly toxic nature of ethylene oxide and its classification as a suspected carcinogen by the National Institute for Occupational Safety and Health (NIOSH), special precautions must be taken to insure safe exposure levels to human receptors.

The Occupational Safety and Health Administration (OSHA) has a standard for worker exposure to ethylene oxide of 50 ppm as a time-weighted average (TWA) concentration for an eight-hour work shift. However, recently, due to the availability of additional data on potential carcinogenicity, OSHA proposed a new, more stringent standard of 1 ppm. It is expected that this proposed standard will be promulgated in 1984.

The major source of olefin oxide worker exposure in the plant is product degassing after removal of the product from the sterilizer. Different types of product absorb or entrap olefin oxide at different levels depending upon the nature of the product, e.g., physical dimensions and exposed surface areas of materials, the specific materials of construction, how the product is packaged and the specific sterilization cycle to which the product was exposed. Unfortunately, not all the absorbed or entrapped olefin oxide is removed in the sterilizer post-evacuation cycle. Hence, the remaining olefin oxide will degass after the product is removed from the sterilizer.

This degassing process can be relatively slow at typical plant ambient conditions and usually necessitates that the product be quarantined for a period of time. The requirement for product quarantining causes additional olefin oxide exposure to workers involved in transferring sterilized product into and out of the quarantine areas. The extent of product holding time in quarantine can also have a significant impact on product inventory requirements at the plant.

In order to reduce worker exposure to olefin oxide as a result of sterilized product degassing, it is first necessary to optimize the post-evacuation cycle. This will enable most of the olefin oxide to be removed from the product while it is still in the sterilization chamber. Time availability, however, usually places limitations on post-evacuation cycle length. Hence, product, when finally removed from the sterilizer, can still pose a worker exposure problem because of degassing. The answer to this problem is continuous aeration with hot air for extended periods of time in separate degassing rooms.

The use of heat to accelerate the olefin oxide degassing process is known. Unfortunately, the use of hot degassing rooms still does not eliminate the worker exposure problems since pallets must be constantly transported into and out of the room. Moreover, heating and ventilation requirements for these hot degassing rooms are relatively high and can be quite expensive, even with energy recovery included. The use of a hot degassing room also means that all sterilized product at the plant will be degassed under the same conditions. Conventional room design precludes optimization of the degassing process for different products. For example, shelf life problems may limit the maximum temperature to which a specific product can be exposed in the hot degassing room. Hence, this same temperature limitation would automatically apply to all other products in the room.

The use of hot degassing tunnels built directly adjacent to the sterilizer have also been used. In this arrangement, pallets are semi-automatically removed from the back of a double-doored sterilizer and transported into the tunnel. However, workers must still enter the tunnel to remove product and heating and ventilation requirements can still be quite high, although not as high as in a hot degassing room. Moreover, the tunnel must be built directly behind the sterilizer, the sterilizer must be double-doored and have a means to automatically or semiautomatically remove the pallets from the sterilizer and transport them into the tunnel. Furthermore, the maximum allowable degassing time is limited to the length of the sterilization cycle which in many cases does not provide sufficient time for acceptable degassing. Such limitations have prevented their widespread use.

SUMMARY OF THE INVENTION

It is an object of the present invention to provide an apparatus to accelerate the degassing of residual olefin oxide from a sterilized product.

It is a further object of the present invention to provide a modular apparatus dedicated to a specific sterilizer and its product load.

It is another object of the present invention to provide an apparatus to sequentially allow pallets of product containing residual olefin oxide to pass through a cell on gravity conveyors.

It is yet a further object of the present invention to provide an apparatus to control the heat, air exchange rate and retention time of a product being conveyed through a cell for the removal of residual olefin oxide such as ethylene oxide or propylene oxide.

The present invention accomplishes the above objects and provides an apparatus which eliminates all of the aforementioned limitations previously associated with the hot degassing of sterilized products. The apparatus enables the use of heat, air exchanges and retention times which permit the degassing process to be optimized for the characteristics of a particular sterilizer load.

The present invention includes a dedicated apparatus for degassing of a sterilized product from a predetermined sterilizer. The apparatus operates independently of the sterilizer and sterilization cycle. The apparatus comprises a cell for degassing a sterilized product. The cell includes at least one conveyor in the cell for conveying the product through the cell. The conveyor is inclined for gravitational movement of the product through the cell. A plurality of stops are disposed along the conveyor for holding the product in the cell at a predetermined position for proper heat transfer. The apparatus also includes air ducts for passing air into the cell and exhausting air from the cell, an air heater for heating air passed through the cell, and doors for isolating the cell during the degassing of the sterilized product.

DETAILED DESCRIPTION OF THE DRAWINGS

Figure 1:
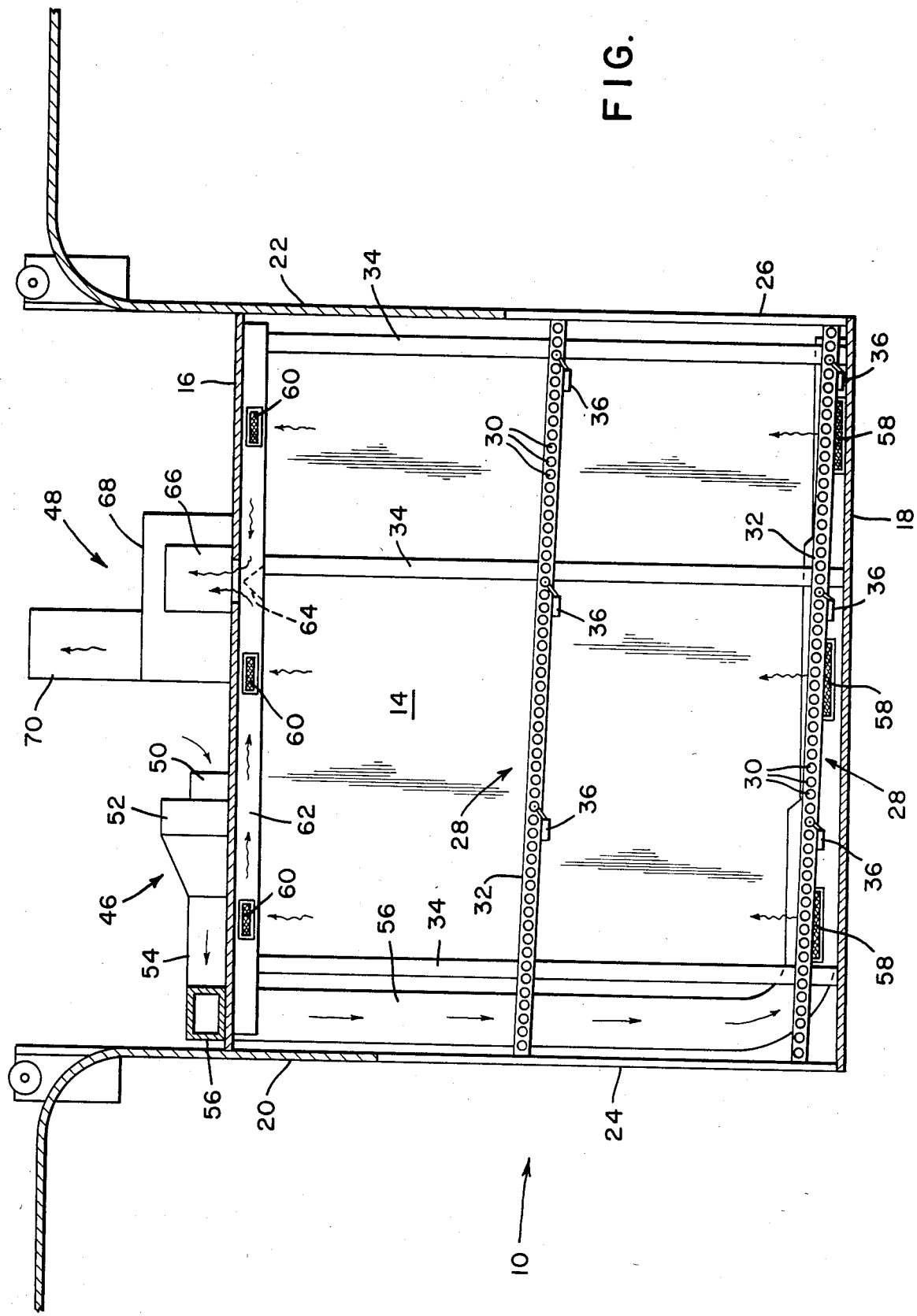
FIG. 1 is a cross-sectional side view of a degassing chamber taken along the lines 1—1 of FIG. 3.

The cell of the present invention comprises a housing 10 having two side walls 12 and 14, a roof 16, and a floor 18 and two doors 20 and 22. The doors 20 and 22 are garage type doors which seal the ends of the cell when closed and are individually raised along guiding tracks 24 and 26, respectively, to an open position. The doors are guided in guide tracks mounted closely to the ends of the side walls. The closed doors form a substantially air tight seal with the side walls.

Two parallel inclined conveyors 28 are mounted in the housing one positioned above the other. The conveyors 28 include a series of parallel rolls 30 spaced slightly apart from each other. The ends of each roll 30 are rotatably mounted in a supporting bracket 32. The supporting brackets 32 are secured to the side walls 12 and 14. The bottom conveyor 28 is placed near the floor 18, slightly above the inlet air vents. The air vents are arranged opposite each other at the bottom of the side walls 12 and 14. The top conveyor 28 is placed approximately half way up each side wall. Both conveyors 28 are inclined downwardly and also extend from the front door 20 to the rear door 22. Upright support beams 34 are attached opposite each other adjacent to side walls 12 and 14. The conveyors 28 are attached to three upright support beams at each side of the housing 10. One set of support beams 34 is positioned opposite each other at the front door end of the housing, one set of support beams is positioned opposite each other at the rear door end of the housing and a third set of support beams is positioned opposite each other between the other two sets of support beams. Each upright support beam 34 is mounted along side walls 12 and 14 between the floor 18 and the roof 16.

Mounted along the length of each of the conveyors 28 are three stops 36. Each of the stops have a cylinder 38, a plunger 40 and an arm 42 connected to the plunger. Connected to the arm 42 is a stop roll 43 mounted on a short arm 44. The stops 36 are activated to stop the movement of an object rolling along the inclined conveyors 28. Cylinders 38 activate the extension of plungers 40. The arm 42 pivots and moves a stop roll 43 into and out of alignment with the rolls 30 in the conveyors 28. When the plunger 40 is extended, the stop roll 43 is raised above the level of the rolls 30 in the conveyor, with the stop roll acting as a stop. When the plunger 40 is retracted the stop roll 43 is aligned with the other rolls 30 of the conveyors 28 in the same spaced relationship as exists between the other rolls 30 of the conveyor. The stop rolls extend between the two mounting brackets 32. The pallets are moved across the conveyors 28 by a sequential lowering of the stop rolls 43, allowing movement of the pallets along the inclined conveyors 28.

On top of the roof 16 of the cell is located the air intake heating system 46 and exhaust system 48. The intake system includes an air feed duct 50. A heater 52 is connected to the air feed duct. Connected to the heater is an air distributing duct 54. The air distributing duct 54 splits into two sections 56, both sections are positioned on the roof 16 and then pass into the housing along the side walls 12 and 14 and bottom wall 18. The air distributing duct is mounted along a bottom edge of each side of the housing. The air distribution duct 54 at the bottom of each side wall has three outlet vents 58.

The exhaust system 48 includes exhaust vents 60 mounted on an exhaust duct 62. The exhaust duct has a diverting plate 64. The exhaust duct is connected to right angle stack 66 connected to an exhaust fan duct 68. The exhaust fan duct 68 is connected to an exhaust stack 70. The air intake system 46, located on the roof 16 near the front door 20 draws in air as a result of the exhaust fan 68 drawing air out of the cell. The air drawn in is first heated and then channelled along the inside of the side walls in the air distribution duct 54 and enters through screened outlet vents 58 disposed along the bottom of each side wall 12 and 14. The outlet vents 58 are located below the bottom inclined gravity conveyor.

The exhaust fan 68, mounted on the roof 16 near the center of the roof, draws air out of the cell through screened air exhaust vents 60. The exhaust duct 62 is mounted on the inside roof of the housing. The exhaust duct 62 has a diverting plate 64 mounted in the exhaust duct for deflecting the exhaust air up into the right angle stack 66 as the air travels in the exhaust duct. The constant drawing in of air by the exhaust fan creates a negative air pressure within the housing. In FIG. 1, arrows indicate the path of travel of the air.

The operation of the present invention will now be described with respect to FIGS. 1-3. At the conclusion of a sterilization cycle, a front roll-up door 20 of a preprogrammed hot degassing cell, located in a sterilizer area, opens. The back roll-up door 22 remains closed. The ventilation fan 68 for the cell is "on" so that any ethylene oxide degassed from the product on the pallet being placed in the cell is captured. The pallet is placed on one of two gravity conveyors 28 shown in FIGS. 1 and 3, where the pallets slowly roll to a pre-selected position. The pre-selected position is established by automatically controlled stops 36 appropriately located on the gravity conveyors 28. The stops 36 are electrically connected to an electric photocell sensing system (not shown).

Figure 2:
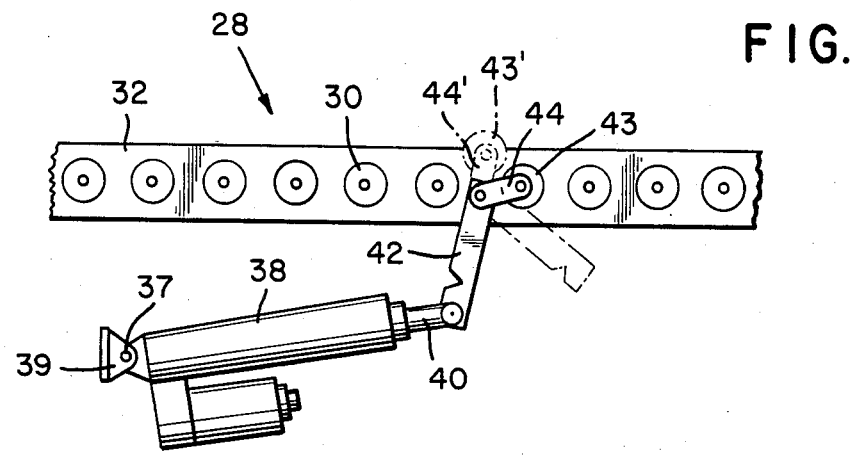
FIG. 2 is a side view of a pop-up stop.
Figure 3:
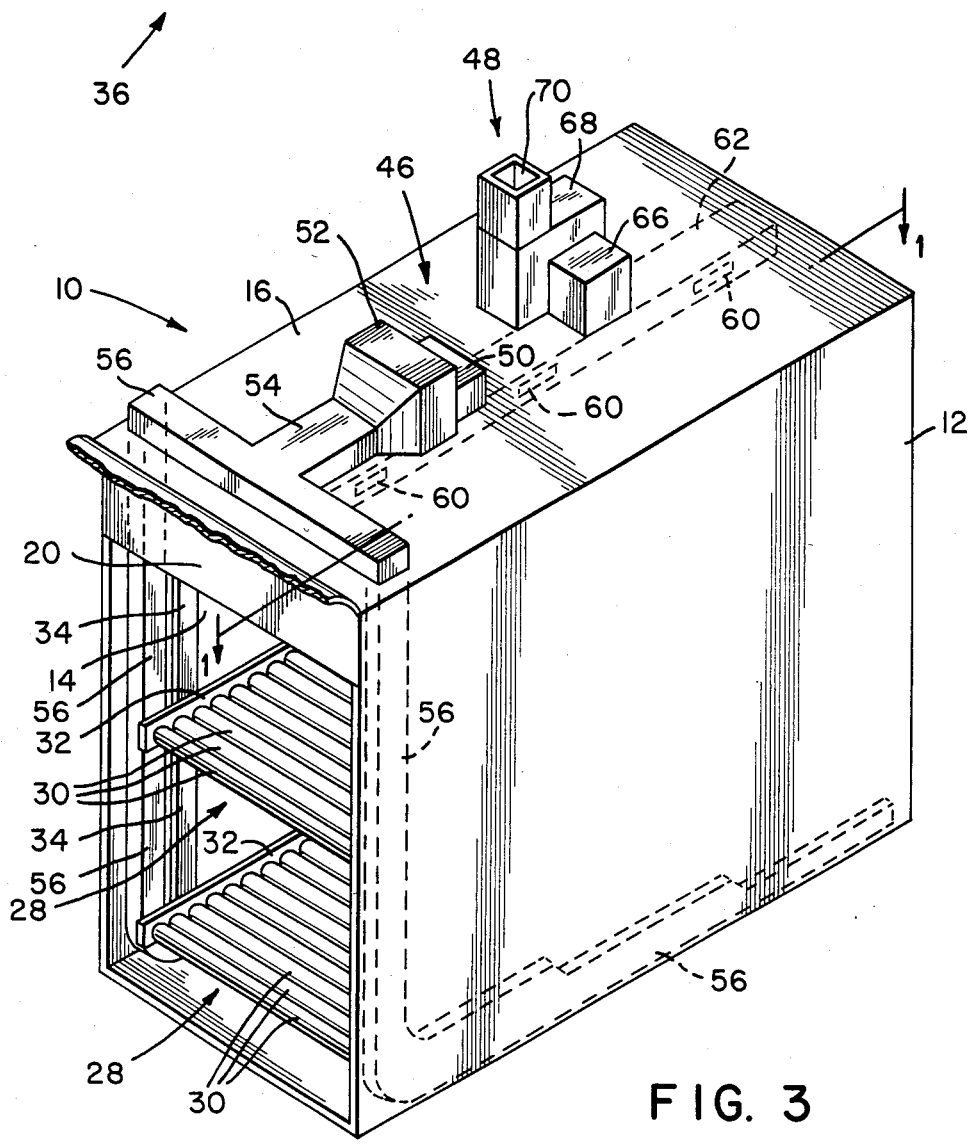
FIG. 3 is a perspective view of a degassing chamber.

Stop 36 is best shown in FIG. 2 wherein a cylinder 38 is pivoted about pin 37 held in a bracket 39. The bracket 39 is secured to a stationary support such as a side wall 12. A plunger 40 of cylinder 38 is coordinated with a light beam from the photocell which is positioned uphill from the stops 36 along the inclined conveyors 28. The plunger 40 is actuated to stop the gravitational movement downhill of a pallet containing sterilized products as signalled by the photocell. When the photocell signals that a pallet is to be stopped, plunger 40, connected to arm 42, is extended. Arm 42, when in phantom position 42' pivots arm 43 holding stop roll 43 to their phantom positions 43' and 44'. Stop roll 43 is now disposed above the plane of the rolls 30 of conveyor 28 and effectively blocks continued downhill movement of a pallet to space one pallet from another. When stop roll 43 is returned to a position in a plane with the rolls 30 of conveyor 28, it is positioned so that a pallet may roll over it.

The conveyors 28 within the cell are arranged in a parallel two tier system. The most advantageous use of space for heating and venting for the degassing of an ethylene oxide sterilized product warrants this construction rather than a long flat tunnel of the same cubic footage. The cell of FIG. 1 was designed for holding 6 pallets but this number may be varied, for example, to a 4, 8, 10, 12, 20, etc. pallet system, and operation made compatible with specific product and degassing requirements.

After the cell is loaded with the pallets from a specific sterilizer load, the front door 20 closes. Air entering the cell is then heated by a gas, steam or electric heater in housing 52 located on the roof on the cell, adjacent to the exhaust fan 68. The air temperature, air flow rate and pallet retention time in the cell are pre-selected and programmed through a programmable controller to optimize the degassing process for the specific sterilizer load.

Air is drawn in through inlet 50, positioned upstream of heater 52. The air is sucked into the cell past heater 52 by the action of the exhaust fan 68 drawing air through the cell. The air flows in through duct 50 past heater 52 and into hot air duct 54. Duct 54 splits into two heating ducts 56. The structure of duct 56 as shown in FIG. 3 is repeated on the opposite side of the cell. Hot air duct 56 extends along an inside edge of the cell, down to the floor 18 of the cell as shown in FIG. 3. Each duct 56 has three internal air outlets 58 disposed along the duct 56. The outlets 58 allow air to enter the cell below the track of the bottom conveyor 28. The outlets 58 are arranged progressively closer to a bottom edge of the cell in order to maintain a constant distance below the bottom conveyor 28.

The exhaust fan 68 remains "on" throughout the process and draws heated air into the cell. The stop rolls 43 on the gravity conveyors 28 locate the pallets in their optimum position for proper air distribution, heat transfer to the pallet and gas removal. The air enters the cell below the track of the bottom conveyor 28 and is sucked up past the bottom tier conveyor and subsequently through the top tier conveyor.

The air entering the cell through outlets 58 is drawn up through the cell by the action of exhaust fan 68. The air being drawn up enters exhaust vents 60 disposed along out-take duct 62 as shown in FIGS. 1 and 3. The exhaust air in duct 62 diverges upward upon hitting V-shaped divertor 64. The air is deflected up into right angle stack 66, through fan 68 and up exhaust stack 70. At the conclusion of the degassing cycle, while front door 20 remains closed, the pre-programmed back door 22 of the cell opens and the pallets are removed one by one as they roll through the rear opening. The doors 20 and 22, as shown in FIG. 1, are both shown in a partially open position. It is intended that when either of the doors are open, the other door is in a closed position. The doors 20 and 22 are of a garage type door sliding along a track 24 and 26 suspended perpendicular to the closed position of the door. The ventilation fan 68 for the cell remains "on" while the pallets are being removed. The workers are never required to enter the cell to withdraw a sterilized load due to the gravity conveyors. There is a minimum of internal moving parts requiring maintenance or repair, thereby virtually eliminating any necessity for entry into the cell.

The cell, including the doors, is completely insulated to minimize heat loss and energy requirements. The doors are designed for minimum air infiltration to minimize internal cell cooling by dilution. The cell is maintained under negative pressure at all times to eliminate the possibility of releasing degassed olefin oxide into the work place especially during loading. Moreover, the area within the hot degassing cell or cells is usually arranged such that the front part of the cell is isolated, possibly by external partitions (not shown), from the back part. The front door 20 of the cell opens in the sterilizer area which is a regulated, controlled access area. The back door 22 opens to the product storage area and to a quarantine area, if still necessary. The latter may or may not be a regulated area, depending upon the effectiveness of the hot degassing process.

A preferred air temperature for a product to be degassed of residual olefin oxide is identical to its exposure temperature during sterilization, typically about 110° to 130° F., a preferred retention time is between about 8 and 24 hours, more preferably between about 16 and 24 hours, and a preferred air exchange rate is about 50 to 60 times per hour. These parameters will vary according to the particular type of product and quantity of product to be degassed.

The cells are modular in design and construction for flexibility and variety in use and are capable of being connected side-by-side in a cellular fashion, depending upon the number of sterilizer loads being handled in a specific time period. The cells are capable of being expanded by adding additional cells connected to a common wall. The size of the cell is such that each cell is dedicated to a particular type of sterilizer load. There is a minimum internal volume for the number of pallets being degassed in the cell. The cells are therefore each operated at the optimum degassing time, temperature and air exchange rate for individual sterilizer loads. The dimensions of a cell are chosen according to the minimum internal volume for the particular product to be sterilized. Therefore, any particular type of sterilizer load can be provided with a cell chosen from a variety of sizes. This significantly minimizes both heating and ventilation requirements and keeps operating costs to a minimum. Cells are easily located and transportable in the event that plant requirements change.

Having described the invention, many modifications thereto will become apparent to those skilled in the art to which it pertains without deviation from the spirit of the invention as defined by the scope of the appended claims.

I claim:

1. A dedicated apparatus for degassing a sterilized product from a predetermined sterilizer, said apparatus operating independently of said sterilizer and sterilization cycle, said apparatus comprising:
   a cell for degassing olefin oxide from a sterilized product;
   at least one conveying means in said cell for conveying said product through said cell, said conveying means being inclined for gravitational movement of said product through said cell;
   a plurality of stop means disposed along said conveying means for holding said product at a predetermined position for flow of air therebetween;
   air handling means for forcibly drawing air into said cell and forcibly exhausting air from said cell to maintain a negative air pressure therein;

air heating means for heating air forced into said cell before air is exhausted from said cell by said air handling means, said air heating means and said air handling means maintaining the air throughout said cell at a pre-selected temperature; and means for isolating said cell during the degassing of said sterilized product.

2. An apparatus as claimed in claim 1, wherein said cell has two end walls, two side walls, a floor and a roof.

3. An apparatus as claimed in claim 1, wherein said means for isolating are positioned for entry and exiting of said product.

4. An apparatus as claimed in claim 2, wherein said at least one conveying means is positioned between said end walls and said side walls.

5. An apparatus as claimed in claim 4, wherein there are two conveyor means parallel to each other.

6. An apparatus as claimed in claim 1, wherein said product is sterilized with ethylene oxide.

7. An apparatus as claimed in claim 1, wherein said product is sterilized with propylene oxide.

8. An apparatus as claimed in claim 2, wherein a plurality of outlets of said air handling means are positioned along said side walls.

9. An apparatus as claimed in claim 2, wherein an air exhaust duct of said air handling means is positioned inside said cell, positioned on said roof.

10. An apparatus as claimed in claim 1, wherein said cell is modular.

11. An apparatus as claimed in claim 2, wherein said means for isolating is positioned between said side walls, said floor and said roof.

12. An apparatus as claimed in claim 2, wherein said air handing means being positioned to move air from said bottom of the cell to said roof of the cell.

* * * * *